United States Patent [19]

Sargent et al.

[11] Patent Number: 4,895,990

[45] Date of Patent: Jan. 23, 1990

[54] FLUORINATED POLYCYCLIC COMPOUNDS

[75] Inventors: Colin R. Sargent; David E. Wotton, both of Bristol, Great Britain

[73] Assignee: I.S.C. Chemicals Limited, London, England

[21] Appl. No.: 66,709

[22] Filed: Jun. 24, 1987

[30] Foreign Application Priority Data

Jun. 24, 1986 [GB] United Kingdom ............... 8615400

[51] Int. Cl.[4] .............................................. C07C 19/08
[52] U.S. Cl. ..................................... 570/130; 228/42; 228/218
[58] Field of Search ......................................... 570/130

[56] References Cited

U.S. PATENT DOCUMENTS

| | | | |
|---|---|---|---|
| 2,459,780 | 1/1949 | McBee et al. | 570/130 |
| 3,962,358 | 6/1976 | Halasz | 570/134 |
| 4,113,435 | 9/1978 | Lagow et al. | 570/130 |
| 4,446,068 | 5/1984 | Mitsch | 570/134 |
| 4,453,028 | 6/1984 | Lagow | 570/130 |
| 4,549,686 | 10/1985 | Sargent et al. | 570/130 |
| 4,739,112 | 4/1988 | Szuu | 570/130 |
| 4,801,761 | 1/1989 | Bailey et al. | 570/130 |

FOREIGN PATENT DOCUMENTS 79187 5/1982 Japan ................................ 570/130

*Primary Examiner*—J. E. Evans
*Attorney, Agent, or Firm*—Fleit, Jacobson, Cohn, Price, Holman & Stern

[57] ABSTRACT

A fully-fluorinated and fully saturated fluorocarbon, containing at least two condensed or non-condensed six-membered rings, seventeen carbon atoms and from 28 to 32 (inclusive) fluorine atoms in its molecule, and having a boiling point from 250° to 265° C.; provided that where the rings are non-condensed they are separated by not more than 4 carbon atoms. Such multi-ring $C_{17}$ saturated-perfluorocarbons are produced by the saturation fluorination of the corresponding multi-ring hydrocarbons and are suitable for use as high-temperature vapour-soldering fluids, especially for use with solders melting above 200° C.

3 Claims, No Drawings

FLUORINATED POLYCYCLIC COMPOUNDS

This invention relates to novel fluorinated polycyclic compounds, suitable for use as high-temperature heat-transfer and working fluids.

There is a need for heat transfer fluid boiling at 250°–265° C. for use in the electronics industry, especially for use in the technique known as "vapour-phase soldering" or "condensation re-flow soldering". (See "Tin and its Uses", No. 130 (1981), p. 1–3). Where solders melting appreciably above 200° C. are employed, e.g. tin-rich solders, then it is necessary to employ a liquid boiling at least 25° C. above the solder melting temperature. However, the liquid employed must not only have a suitable boiling point or boiling range, it must also be thermally stable and not decompose in the presence of metals or plastics materials. A further constraint on the fluid is that it must not soften P.T.F.E. or similar materials used in electronic circuit boards. It must also not produce toxic decomposition products at high temperatures.

The present invention particularly relates to a fluid suitable for use in such high-temperature heat transfer applications as vapour phase soldering at 250°–265° C.

We are aware that there is known from J. App. Chem., 1952, Vol 2, page 127, a fully saturated fluorocarbon produced from diphenyl pentane, i.e. where two cyclohexyl rings are linked by a $C_5$ carbon chain. There is no disclosure or suggestion that this compound is useful as a high temperature transfer fluid.

According to a first aspect of the invention, there is provided a fully-fluorinated, fully-saturated fluorocarbon containing a plurality of rings and 17 carbon atoms in its molecule and having a boiling point from 250° to 265° C., for use in high temperature transfer processes in general and in vapour phase soldering in particular. Such a compound can be produced from a suitable hydrocarbon starting material by total fluorination to saturate the molecule, e.g. using cobalt trifluoride or caesium tetrafluorocobaltate at a temperature of 300–400° C. A suitable process is described in Tetrahedron 1963, Volume 19, pages 1893 to 1901.

More specifically, the invention provides a fully-fluorinated and fully saturated fluorocarbon, containing at least two condensed or non-condensed six-membered rings, seventeen carbon atoms and from 28 to 32 (inclusive) fluorine atoms in its molecule, and having a boiling point from 250° to 265° C.; provided that where the rings are non-condensed they are separated by 1 to 4 carbon atoms.

The saturated fluorocarbons of this invention are the compounds produced by saturation fluorination of the $C_{17}$ hydrocarbons described below and as such have the corresponding carbon skeletons. Thus, the description of suitable hydrocarbons for this process also defines the structures of the fluorocarbons. In each case it is to be understood that fully or partially reduced derivatives of the hydrocarbon named may be employed to give a fluorocarbon of the same structure. The fluorocarbon may have a molecular formula $C_{17}F_{28}$, $C_{17}F_{30}$ or $C_{17}F_{32}$ depending on the number and type of rings present.

Suitable hydrocarbons may be any $C_{17}$ fused polycyclic compound, including 7H-benzanthracene (I), 1H-benzanthracene (II), 3H-benzanthracene (III), benzofluorene (IV), benzofluorene (V) benzofluorene (VI), and the isomers of cyclopentaphenanthrene and cyclopentanthracene.

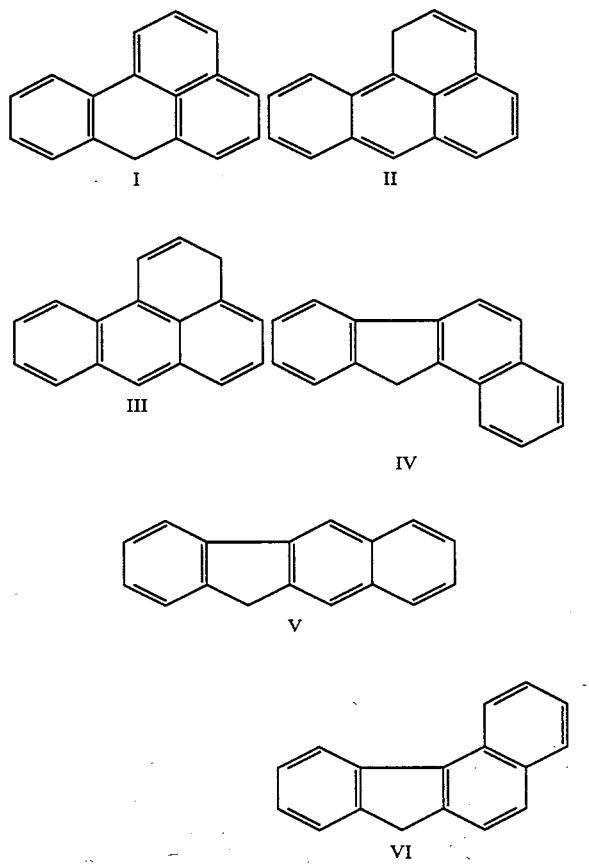

Thus the fluorocarbon compound according to the invention may be suitably based on a benzanthracene, benzofluorene, cyclopentaphenanthrene or cyclopentanthracene nucleus.

A second type of suitable hydrocarbon contains 17-n carbon atoms in a fused polycyclic nucleus (where n is from 1 to 7 inclusive) and is substituted with one or more alkyl, alkenyl or alkynyl groups containing a total of n carbon atoms to bring the total number of carbon atoms in the molecule to 17. Where alkyl groups are present they should preferably be n-alkyl groups since branched side-chains lead to increased fragmentation during the fluorination stage and give less thermally stable fluorocarbon products. In the final product any alkenyl or alkynyl groups present in the starting hydrocarbon will have been converted to alkyl groups.

Thus further preferred fluorocarbon compounds of the invention have n as defined and their nucleus is a saturated polycyclic ring system.

Thus, when $N = 1$, the hydrocarbon may be a substituted preferably methyl-substituted, derivative of fluoranthene (VII), pyrene (VIII), a benzobiphenylene such as 1,2-benzobiphenylene (IX) or 2.3-benzobiphenylene (X), or a dibenzopentalene such as 1,2,4,5-dibenzopentalene (XI).

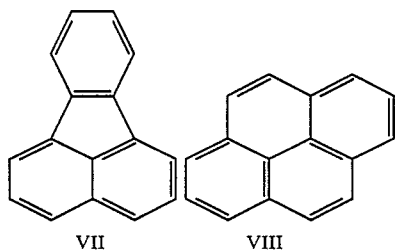

VII  VIII

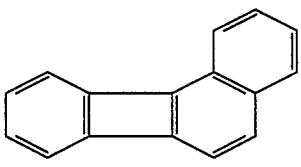

IX

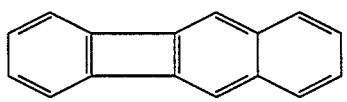

X

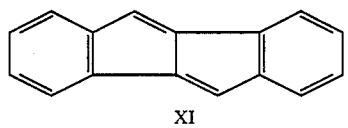

XI

When n=2, the polycyclic C₁₅ nucleus may be a methylenephenanthrene such as 4,5-methylenephenanthrene (XII).

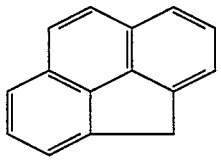

XII

When n=3, the polycyclic C₁₄ nucleus may be phenanthrene (XIII) or anthracene (XIV).

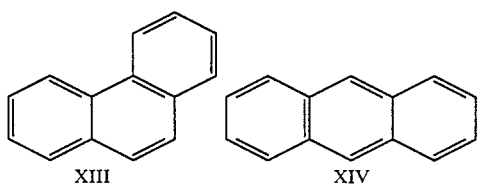

XIII  XIV

When n=4, the polycyclic C₁₃ nucleus may be fluorene (XV), perinaphthene (XVI), or a benzindane such as 4,5-benzindane (XVII) or 5,6-benzindane (XVIII).

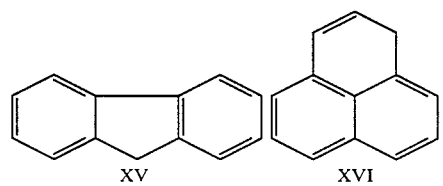

XV  XVI

-continued

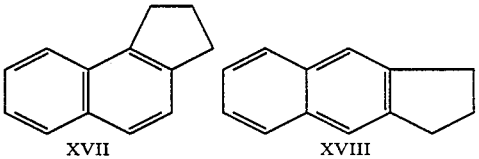

XVII  XVIII or the corresponding benzindenes.

When n=5, the polycyclic C₁₂ nucleus may be acenaphylene (XIX) or biphenylene (XX).

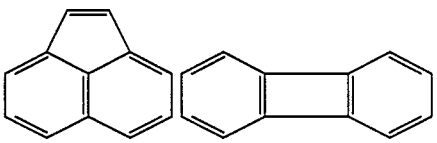

XIX  XX

When n=7, the polycyclic C₁₀ nucleus may be naphthalene or azulene.

A third type of suitable C₁₇ hydrocarbon contains two or more ring systems separated within the molecule. This type includes diaryl methanes in which two aryl groups are separated by a -CH₂- link, including 1- and 2-benzylnaphthalene (XXI and XXII), 5- and 6-benzyl-tetralin (XXIII and XXIV), and derivatives of the C₁₃ compound diphenyl-methane substituted with one or more alkyl, alkenyl or alkynyl groups containing a total of 4 carbon atoms, e.g. 4 methyl groups.

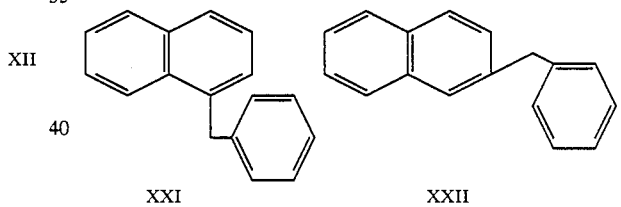

XXI  XXII

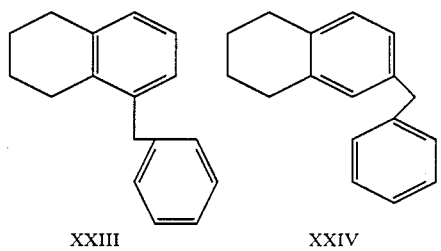

XXIII  XXIV

The hydrocarbon may also be a derivative of the C₁₄ hydrocarbon 1,2-diphenylethane, substituted with one or more alkyl, alkenyl, or alkynyl groups containing a total of 3 carbon atoms; a derivative of the C₁₅ hydrocarbon 1,3-diphenylpropane, substituted with two methyl groups, an ethyl group or a vinyl group; or a derivative of the C₁₆ hydrocarbon 1,4-diphenylbutane, substituted with methyl.

The hydrocarbon may also contain two aryl groups joined directly by a single carbon-carbon bond. This includes methyl substituted derivatives of the C₁₆ hydrocarbons 1- and 2-phenylnaphthalene (XXV and XXVI)

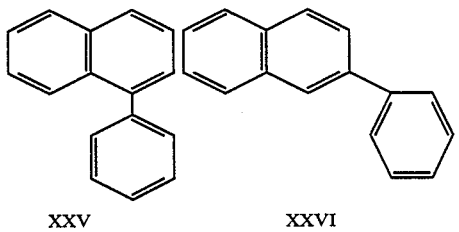

XXV  XXVI and derivatives of the $C_{12}$ hydrocarbon biphenyl (XXVII) substituted with one or more alkyl, alkenyl or alkynyl groups containing a total of 5 carbon atoms.

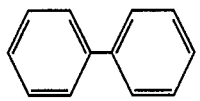

XXVII

A preferred compound is perfluoroperhydrobenzanthrene of molecular formula $C_{17}F_{28}$ having 4 condensed 6-membered rings in its structure. The boiling range of this compound is 259.5°–263.5° C.

This new compound perfluoroperhydrobenzanthrene can be produced from a known starting material, benzanthrene (I), by total fluorination as described above.

Perfluoroperhydrobenzanthrene has the structural formula (XXVIII):

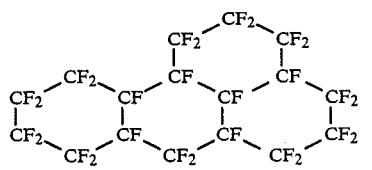

XXVIII it being understood that this embraces a large number ($2^6$) of cis/trans isomers.

Another suitable fluid can be produced in a similar manner from isomers of the known hydrocarbons benzylnaphthalene (XXI nd XXII) and benzyl-tetralin (XXIII and XXIV) or mixtures thereof. This fluid is herein referred to as perfluoro(bicyclodecyl)cyclohexyl methane, $C_{17}F_{30}$, and consists of a mixture of a number of the possible stereo- and structural isomers of perfluoro(bicyclodec-2-yl)cyclohexylmethane (XXIX) and perfluoro(bicyclodec-3-yl)cyclohexylmethane (XXX) and boils in the range 257–259° C. *

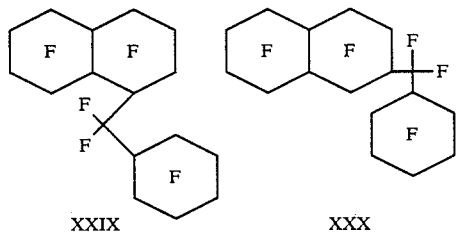

XXIX  XXX

Other particularly preferred compounds according to the invention are:
perfluorobis(dimethylcyclohexyl)methane, $C_{17}F_{32}$, of boiling range 258–262° C.
perfluoro(9-butylperhydrofluorene), $C_{17}F_{30}$, of boiling range 250–252° C.

According to a second aspect, the present invention provides a method of soldering wherein a component to be soldered, using a solder melting above 200° C., is immersed in a vapour bath to melt the solder, and the component is then withdrawn from the bath, characterised in that the vapour bath is composed predominantly of the vapour of a fully-fluorinated, fully-saturated fluorocarbon having at least two six-membered rings, seventeen carbon atoms and from 28 to 32 fluorine atoms, in its molecule, and a boiling range within the limits 250°–265° C. Preferably the fluorocarbon is as defined according to the first aspect of the invention, in that non-condensed rings are separated by not more than 4 carbon atoms.

The invention will be further described with reference to the following illustrative examples.

EXAMPLE 1 Preparation and Characterisation of Perfluoroperhydrobenzanthrene

Benzanthrene was melted into a stream of nitrogen and was fed into a stirred cobalt fluoride reactor (as described in Advances in Fluorine Chemistry, by Stacey, Tatlow and Sharpe, Butterworths, (1960), Vol. 1, pages 166 et seq) which was maintained at 350°–360° C. A liquid product was produced. After filtering, washing and drying, the crude product was further worked-up and purified as follows:

The crude fluorocarbon (118 g.) was put into a 100 ml round-bottomed flask which was fitted with a thermocouple pocket and an air bleed. The product was then fractionally distilled up a 300×15 mm column which was packed with 1/16 inch×1/16 inch stainless steel Dixon gauzes. The distillation was at a reduced pressure of 18–22 mm Hg. A number of fractions were obtained, of which fraction 4 had the following physical properties:

| Fraction | Weight (g) | B.Pt. (°C.) | Pressure (mm Hg) | B.pt. at 760 mm (°C.) |
|---|---|---|---|---|
| 1 | 34.6 | 140–143 | 18–21 | 263.5 |

Fraction 4 was then subjected to mass, infrared, and n.m.r. spectroscopy, and elemental analysis. The following results were obtained.

Mass Spectrometry

M/e - 736 ($C_{17}F_{28}$) with a fragmentation pattern consistent with that expected for perfluoroperhydrobenzanthrene.

Infrared Spectrum

This showed no detectable CH bonds, and was consistent with the proposed structure.

N.m.r Spectrum

The $^{19}F$ spectrum showed groups of signals from —$CF_2$ groups ($\delta$ 105–144 ppm) and from tertiary atoms (—$\overset{|}{\underset{|}{C}}F$ groups: $\delta$ 175–188 ppm)

in approximately the correct ratio (22.6) for the proposed structure, ($C_{17}F_{28}$).

Chemical Analysis

Found : C,27.9%; F, 71.8% Calculated for $C_{17}F_{28}$ : C, 27.7%; F 72.3%

EXAMPLE 2

Vapour-Phase Soldering Using Perfluoroperhydrobenzanthrene

A test sample was prepared by pushing a 6 inch length of 1/16 inch diameter round brass rod (polished) into a 1/16 inch hole drilled in the centre of a dished ⅜ inch diameter disc of polished copper sheet, 10 thousandths of an inch thick. After assembly of the test piece, the dished copper disc was located at right angles to the brass rod, about 1/2 inch from one end. A number of these units were fabricated.

5-10 cc of the liquid under test (Example 1, fraction 4) was poured into a 1 inch borosilicate glass boiling tube, and a few anti-bumping granules were added. The liquid was boiled on a microburner at such a rate that the vapour condensed on the walls of the tube up to about 3/2 inch above the liquid surface.

The test pieces were prepared by holding the brass wire vertical, with the copper disc near the lower end, and placing a layer of solder or soldering paste on top of the copper disc, covering the upper surface.

The upright test piece was then lowered down the boiling tube, until the copper disc was immersed in the vapour layer of the boiling liquid. It was then held there until the solder had melted and bonded to the brass and copper (about 10 seconds). The test piece was then removed, cooled, and the quality of the joint was assessed.

The following table shows the results obtained with three "Multicore*" soldering compounds:

| Solder Grade | Solder Composition | Solder m.pt. °C. | Quality of joint |
|---|---|---|---|
| Multicore* 95A | 95% Sn, 3% Sb | 236-243 | Good |
| Multicore* 96S | 96.3% Sn, 3.7% Ag | 221 | Good |
| Multicore* PT | Pure tin | 232 | Good |

*Multicore is a registered trade mark

A good joint was also obtained using pure tin as solder, with phosphoric acid as flux.

EXAMPLE 3

Preparation and Characterisation of Perfluoro(bicyclo decyl)cyclohexylmethane (Isomeric Mixture)

A mixture of 5- and 6-benzyl-1,2,3,4-tetrahydronaphthalene (readily prepared by Friedel-Crafts benzylation of tetralin), was fed into a cobalt trifluoride reactor at 340-360° C. to give crude fluorinated product. After a work-up involving neutralisation, fractional distillation under reduced pressure, and chemical purification, this yielded a fluorocarbon fluid with a boiling point at atmospheric pressure of 257-259° C. and a pour-point of −10° C. Analysis by g.l.c. and g.l.c./mass spectroscopy showed this to be an extensive mixture of closely-related components, probably positional and geometrical isomers of the title compound.

Negative ion, chemical ionisation mass spectroscopy showed the expected parent ion at m/e 774 ($C_{17}F_{30}$) with a fragmentation pattern consistent with perfluoro(-bicyclodecyl)cyclohexylmethane. The $^{19}F$ n.m.r. spectrum showed groups of signals from $-CF_2-$ groups and from

groups in the correct ratio (26:4). The infra-red spectrum was consistent with a mixture of saturated fluorocarbons.

EXAMPLE 4

Soldering Capability Using Tin Solders

A sample of the perfluoro(bicyclodecyl)cyclohexylmethane isomer mixture, boiling range 257-259° C., was tested using the method described in Example 2.

The time taken for the solder to melt and form a seal was then noted.

The procedure was carried out for the following solders:

(a) Multicore Solder Paste : Tin PRA B3
(b) Pure Tin (99.9% Sn) - with a phosphoric acid flux

| | | Results |
|---|---|---|
| Solder | Melt Time (sec.) | Comments |
| Multicore Tin PRA B3 | <10 | Good clean melt - some resin like material on surface of solder. Excellent joint. |
| Pure Tin + $H_3PO_4$ flux | ca. 15 | Fairly good, clean melt. White paste like deposit on surface of solder. Excellent joint. |

EXAMPLE 5

Thermal Stability of Perfluoro(bicyclodecyl)cyclohexyl Methane (Isomer Mixture) at the Boiling Point In order to investigate the corrosivity of the test fluid at levels of high humidity (so simulating actual working conditions), the following test method was devised.

A 500 ml flange necked flask was equipped with a clean copper cooling coil (water cooled). The test fluid (50 ml) was added to clean copper turnings (approximately 5 gm. "Analar" grade) in the flask. In order to simulate 'wet' conditions, which occur when equipment cooling coil temperatures are below the atmospheric dew point, small glass tubes half filled with dionized water and containing metal test strips (one of copper and one of stainless steel) were suspended in the flask space above the cooling coils.

The unit was then heated, using an electric heating mantle, until reflux was achieved. This was maintained for a period of 24 hours. The unit was then allowed to cool to room temperature and each component was examined for signs of corrosion or instability.

Conclusion

Examination of the copper turnings, the glass flask, the copper cooling coil, the test fluid, and the copper and stainless steel test strips, showed negligible corrosion or etching of the metal and glass surfaces. The test fluid showed no significant change by visual inspection, or by analysis by glc, chemical determination of displaceable fluorine, or assay of free hydrofluoric acid.

This test therefore shows that this sample of perfluoro(bicyclodecyl)cyclohexylmethane is suitable for use as a vapour phase soldering fluid.

EXAMPLE 6

Stability to Alkaline Hydrolysis

A sample of the test fluid (perfluoro(bicyclodecyl)cyclohexylmethane, mixed isomers) (10 cm$^3$) was placed in a 100 ml 'Quickfit' conical flask. To this was added 10 cm$^3$ of an alcoholic solution of potassium hydroxide (10% mixture, w/w, of "Analar" grade KOH in "Analar" grade Methanol). A few 'anti-bumping' granules were added and then the flask was fitted with an air condenser. The unit was then placed on a small hot plate, then carefully heated until constant reflux was obtained.

This was maintained for a period of 4 hours after which the KOH/MeOH fraction was analysed for fluoride ion content.

To act as a blank control, an identical unit was maintained under reflux, except the fluorocarbon fluid was omitted.

Conclusion

Negligible fluoride ion was found in the alcoholic liquor. The test fluid was stable to alcoholic potassium hydroxide under the test conditions.

EXAMPLE 7

Preparation and Characterisation of Perfluorobis(dimethylcyclohexyl)methane

A mixture of dixylylmethanes, prepared by the condensation of m-xylene with formaldehyde in the presence of an acid catalyst and consisting principally of bis(2.4-dimethylphenyl)methane, was fed into a cobalt trifluoride reactor operating at 350–360° C. to give crude fluorinated product. After a work-up involving neutralisation, fractional distillation under reduced pressure and chemical purification, this yielded a fluorocarbon liquid with a boiling range of 258–262° C. at atmospheric pressure. Analysis by g.l.c/mass spectroscopy showed this to be an extensive mixture of compounds of closely related structure. The mass spectrum showed a highest mass peak at m/e=774, corresponding to M-2F from the title compound ($C_{17}F_{32}$, M.Wt. 812). The infra-red spectrum was consistent with a mixture of saturated fluorocarbons.

EXAMPLE 8

Soldering Using Perfluorobis(dimethylcyclohexyl)methane

A sample of perfluorobis(dimethylcyclohexyl)methane, boiling range 258–262° C., was tested for soldering capability using Multicore Solder PRA B3 by the method described in Example 2. An excellent joint was produced with a melt time of less than 10 seconds.

EXAMPLE 9

Preparation and Characterisation of Perfluoro-9-butylperhydrofluorene

A sample of 9-n-butylfluorene (See H E Fritz et al, Journal of Organic Chemistry, Vol. 30, 1965, p. 2540) was fed into a cobalt trifluoride reactor operating at 400–450° C. to give a crude fluorinated product. After a work-up involving neutralisation, fractional distillation under reduced pressure, and chemical purification, this yielded a fluorocarbon liquid with a boiling range of 250–252° C. at atmospheric pressure. Analysis by g.l.c. showed this to be an extensive mixture of compounds of closely related structure. G.l.c./mass spectroscopy showed a highest mass peak at m/e=755, corresponding to M-F from the title compound ($C_{17}F_{30}$, M.Wt. 774). The infra-red spectrum was consistent with a mixture of saturated fluorocarbons.

EXAMPLE 10

Soldering Using Perfluoro-9-butylperhydrofluorene

A sample of perfluoro-9-butylperhydrofluorene, boiling range 250–252° C., was tested for soldering capability using Multicore Solder PRA B3 by the method described in Example 2. An excellent joint was produced with a melt time of approximately 10 seconds.

EXAMPLE 11

Preparation and Characterisation of Perfluorocyclohexyl(tetramethylcyclohexyl)methane Benzyl-2,3,4,5-tetramethylbenzene, prepared by the condensation of durene with benzyl alcohol using p-toluene sulphonic acid catalyst, was fed into a cobalt fluoride reactor operating at 310° C. to give crude fluorinated product. After a work-up involving neutralisation and fractional distillation under reduced pressure, this yielded a fluorocarbon liquid with a boiling range of 250–260° C. at atmospheric pressure. Analysis by g.l.c./mass spectroscopy showed this to be a mixture of compounds of closely related structure. The mass spectrum showed a highest mass peak at m/e=755, corresponding to M-3F for the title compound ($C_{17}F_{32}$, M.Wt. 812).

We claim:

1. A fully fluorinated and fully saturated perfluorocarbon, consisting of a diarylmethane derivative containing at least two saturated six-membered rings, condensed or non-condensed, seventeen carbon atoms and from 28–32, inclusive, fluorine atoms, and having a boiling point from 250 degrees C. to 265 degrees C.
2. Perfluorobis(dimethylcyclohexyl)methane, $C_{17}F_{32}$.
3. Perfluoro(bicyclodecyl)cyclohexylmethane, $C_{17}F_{30}$.

* * * * *